(12) United States Patent
Calabrese et al.

(10) Patent No.: US 10,758,709 B2
(45) Date of Patent: Sep. 1, 2020

(54) ARTICULATING DEVICES AND METHODS

(71) Applicant: Boston Scientific Scimed, Inc., Maple Grove, MN (US)

(72) Inventors: Andrew Calabrese, Lancaster, MA (US); Brian Gaffney, Rutland, MA (US); Gene Storbeck, Franklin, MA (US); Mark Wood, Sterling, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 126 days.

(21) Appl. No.: 15/605,635

(22) Filed: May 25, 2017

(65) Prior Publication Data

US 2017/0340862 A1 Nov. 30, 2017

Related U.S. Application Data

(60) Provisional application No. 62/341,982, filed on May 26, 2016.

(51) Int. Cl.
*A61M 25/00* (2006.01)
*A61M 25/01* (2006.01)
*B29C 48/10* (2019.01)
*B29C 48/21* (2019.01)
*A61B 1/00* (2006.01)
*A61B 1/005* (2006.01)

(52) U.S. Cl.
CPC ....... *A61M 25/0141* (2013.01); *A61B 1/0011* (2013.01); *A61B 1/0055* (2013.01); *A61B 1/0057* (2013.01); *A61M 25/005* (2013.01); *A61M 25/0012* (2013.01); *A61M 25/0045* (2013.01); *A61M 25/0147* (2013.01); *B29C 48/10* (2019.02); *B29C 48/21* (2019.02); *A61M 2025/015* (2013.01)

(58) Field of Classification Search
CPC ............ A61M 25/005; A61M 25/0141; A61M 2025/015; A61M 25/0045; A61M 25/0144; A61M 25/0147; A61M 25/0012
See application file for complete search history.

(56) References Cited

U.S. PATENT DOCUMENTS

| | | | |
|---|---|---|---|
| 3,924,632 A | 12/1975 | Cook | |
| 4,425,919 A | 1/1984 | Alston, Jr. et al. | |
| 4,911,148 A | 3/1990 | Sosnowski et al. | |
| 5,005,558 A | 4/1991 | Aomori | |
| 5,025,778 A | 6/1991 | Silverstein et al. | |

(Continued)

FOREIGN PATENT DOCUMENTS

| EP | 2 937 110 A1 | 10/2015 |
|---|---|---|
| WO | WO 2014/203343 A1 | 12/2014 |

*Primary Examiner* — Rebecca E Eisenberg
(74) *Attorney, Agent, or Firm* — Bookoff McAndrews, PLLC

(57) ABSTRACT

Aspects of articulating devices and methods are disclosed. An exemplary articulating device may comprise an interior core with a reinforcing extending along a central axis, an exterior layer bonded to the interior core by an interface, and a lumen extending through the exterior layer, exterior of the reinforcing element, and parallel to the central axis. A steering wire may be moveable in the lumen to articulate a distal end of the device relative to the central axis in response to a force applied to the steering wire. Related methods of manufacturing an articulating device are also described.

19 Claims, 7 Drawing Sheets

(56) References Cited

U.S. PATENT DOCUMENTS

| | | |
|---|---|---|
| 5,037,404 A | 8/1991 | Gold et al. |
| 5,271,382 A | 12/1993 | Chikama |
| 5,313,967 A | 5/1994 | Lieber et al. |
| 5,381,782 A | 1/1995 | DeLaRama et al. |
| 5,477,856 A | 12/1995 | Lundquist |
| 5,480,382 A | 1/1996 | Hammerslag et al. |
| 5,562,619 A | 10/1996 | Mirarchi et al. |
| 5,662,119 A | 9/1997 | Brennen et al. |
| 5,738,742 A | 4/1998 | Stevens |
| 5,795,341 A | 8/1998 | Samson |
| 5,865,800 A | 2/1999 | Mirarchi et al. |
| 5,873,817 A | 2/1999 | Kokish et al. |
| 5,916,147 A | 6/1999 | Boury |
| 5,964,971 A | 10/1999 | Lunn |
| 6,012,494 A | 1/2000 | Balazs |
| 6,068,622 A | 5/2000 | Sater et al. |
| 6,123,699 A | 9/2000 | Webster, Jr. |
| 6,171,235 B1 | 1/2001 | Konstorum et al. |
| 6,450,948 B1 | 9/2002 | Matsuura et al. |
| 6,589,227 B2 | 7/2003 | Sonderskov |
| 6,749,560 B1 | 6/2004 | Konstorum et al. |
| 6,780,151 B2 | 8/2004 | Grabover et al. |
| 6,945,956 B2 | 9/2005 | Waldhauser et al. |
| 6,991,616 B2 | 1/2006 | Bencini et al. |
| 7,011,655 B2 | 3/2006 | Thompson et al. |
| 7,824,392 B2 | 11/2010 | Zhou |
| 7,833,218 B2 | 11/2010 | Lunn et al. |
| 7,922,650 B2 | 4/2011 | McWeeney et al. |
| 8,376,991 B2 * | 2/2013 | Kauphusman .... A61M 25/0012 604/95.04 |
| 8,579,802 B2 | 11/2013 | Robertson |
| 9,039,676 B2 | 5/2015 | Klima |
| 2004/0102719 A1 | 5/2004 | Keith |
| 2005/0015072 A1 | 1/2005 | Engel et al. |
| 2005/0272975 A1 | 12/2005 | McWeeney et al. |
| 2006/0111649 A1 | 5/2006 | Zhou |
| 2007/0016130 A1 | 1/2007 | Leeflang et al. |
| 2008/0091169 A1 | 4/2008 | Heideman et al. |
| 2009/0192495 A1 * | 7/2009 | Ostrovsky ............ A61B 1/0055 604/528 |
| 2012/0123327 A1 | 5/2012 | Miller |
| 2012/0277671 A1 * | 11/2012 | Fuentes ............... A61M 25/005 604/95.04 |
| 2013/0072905 A1 * | 3/2013 | Jansen ................ A61M 25/005 604/525 |
| 2015/0174363 A1 | 6/2015 | Sutermeister |

* cited by examiner

ARTICULATING DEVICES AND METHODS

CROSS-REFERENCE TO RELATED APPLICATIONS

This patent application claims the benefit of priority under 35 U.S.C. § 119 to U.S. Provisional Patent Application No. 62/341,982, filed May 26, 2016, which is herein incorporated by reference in its entirety.

TECHNICAL FIELD

Aspects of the present disclosure generally relate to medical devices and procedures. In particular, aspects relate to articulating devices and methods.

BACKGROUND

Medical devices are commonly used to access remote regions of the body for diagnostic, surgical, or therapeutic purposes. In some examples, endoscopes may be inserted through a body lumen to access the colon, esophagus, stomach, urethra, bladder, ureter, kidneys, lungs, bronchi, uterus, and/or or other organs. In other examples, catheters may be inserted through the circulatory system to access treatment sites near the heart, or through the urinary system to access sites near the kidney.

Body lumens come in various shapes and sizes. Some medical devices may be introduced into the body through a large body lumen (such as the urethra) and passed through a narrower body lumen (such as a ureter) to reach a treatment site (such as the interior of a kidney). Some body lumens are naturally formed to curve, loop around, or even wind back, while other body lumens are surgically formed by tunneling tools and, thus, irregularly shaped. A device with a steerable shaft is advantageous when negotiating any of these body lumens. Such a device should be flexible enough to permit steering, yet rigid enough to prevent buckling.

Wires may be used to steer the device through a body lumen. In some devices, the wires are routed through the interior of the device, potentially increasing its outer diameter. Because the device may be pushed through the body lumen, even small increases in the outside diameter of the device may complicate access to some treatments sites by preventing passage of the device through a preferred body lumen. In other devices, the wires may be routed through a structure inside of the device, such as a sleeve, which may further increase the outer diameter of the device. These structures also may decrease the usable interior space of the device. Given that most body lumens are narrow, even small decreases in the usable interior space of the device may limit its usefulness by, for example, reducing the size of one or more working lumens extending through the device, and/or the type of tool usable therewith.

The articulating devices and methods described herein may rectify some of the deficiencies described above, and address other aspects of the prior art.

SUMMARY

Aspects of the present disclosure relate to articulating devices and methods. Numerous aspects of the present disclosure are now described.

One aspect of this disclosure is an articulating device. The device may comprise an interior core with a reinforcing element extending along a central axis, an exterior layer bonded to an exterior surface of the interior core by an interface, a lumen extending through the exterior layer, exterior of the reinforcing element, and parallel to the central axis, and a steering wire moveable in the lumen to articulate a distal end of the device relative to the central axis in response to a force applied to the wire.

According to this aspect, the interface may comprise a chemical bond or a physical bond formed between the exterior layer and the interior core. A plurality of articulation slots may be defined by an exterior surface of the exterior layer. The interior core may be encased in a first material. The exterior layer may include a second material, and the interface may comprise a fused portion of the first and second materials. An exterior portion of the exterior layer may be made of a third material, an interior portion of the exterior layer may be made of the second material, and an exterior portion of the interior core may be made of the first material. The third material may have a melting point greater than that of the first and second materials. Each of the first, second, and third materials may be a polymeric material, such as a thermoplastic.

The reinforcing element may comprise one or more wires spiraled about the central axis. The one or more wires may be interwoven to form a braided wire tube. The one or more wires may have an exterior surface configured to maximize surface area contact with the first material. The reinforcing material of the interior core may be a first reinforcing element, the exterior layer may comprise a second reinforcing element encased in the second material, and the lumen may be contained between an exterior surface of the core and an interior surface of the second reinforcing material. The lumen may have a cross-sectional shape with a minimum dimension in a direction perpendicular to the central axis. The second reinforcing element may comprise a wire spiraled about the central axis to surround the interior core and the lumen. A portion of second reinforcing element may be interwoven with a portion of the first reinforcing element.

The lumen may comprise a plurality of lumens, the steering wire may comprise a plurality of steering wires, and each of the plurality steering wires may be received in one of the plurality lumens. A cap may be attached to a distal end of each of the plurality of steering wires. A distal end of the interior core and/or a distal end of the exterior layer may be attached to a proximal end of the cap to seal each of the plurality of lumens. A proximal end of each of the plurality of steering wires may be attached to a steering device configured to apply the force.

Another aspect of this disclosure is an articulating device. The device may comprise an interior core extending along a central axis, the core including a reinforcing element encased therein; an exterior layer bonded to an exterior surface of the interior core by an interface, the exterior layer defining a plurality of articulation slots; a plurality of lumens extending through the exterior layer, exterior of the reinforcing element, and parallel to the central axis; and a plurality of steering wires, each steering wire being moveable in one of the plurality of lumens to articulate a distal end of the device relative to the central axis in response to a force applied to one or more of the wires.

According to this aspect, a cap may be attached to a distal end of each of the plurality of steering wires. A distal end of the interior core and/or a distal end of the exterior layer may be attached to a proximal end of the cap to seal each of the plurality of lumens. A proximal end of each of the plurality of steering wires may be attached to a steering device configured to apply the force.

Another aspect of the present disclosure is a method of manufacturing an articulating device. The method may comprise forming an interior core, forming an exterior layer, interfacing the interior core to the exterior layer so as to define a central axis within the interior core and at least one lumen extending parallel to the axis between the interior core and the exterior layer, inserting a steering wire into each at least one lumen, and attaching a distal end of each wire to a cap.

According to this aspect, forming the interior core may comprise extruding a first material through a mold together with a first reinforcing element. Forming the exterior layer may comprise extruding a second material through a mold. The interfacing may further comprises sliding the interior core into the exterior layer, and applying a heat to the interior core and the exterior layer so as to fuse at least a portion of the first material to a portion of the second material. The interfacing may further comprise placing a elongated mold adjacent an exterior surface of the interior core so that each of the plurality of lumens are formed into an interior portion of the exterior layer by the heat.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate exemplary aspects of this disclosure that, together with the written descriptions, serve to explain the principles described herein.

DETAILED DESCRIPTION

Aspects of the present disclosure are now described with reference to exemplary articulating devices and methods. Some aspects are described with reference to a medical procedure, wherein a distal end of an articulating device is steered towards a body cavity, such as the interior of a kidney. During this procedure, said distal end may be steered toward a material in the body, such as a kidney stone formed in the interior of a kidney. Any reference to a particular type of procedure, such as medical; material, such as a kidney stone or portion thereof; or body cavity, such as the interior of a kidney, is provided as an example and not intended to limit the present disclosure unless claimed. Accordingly, the concepts described herein may be utilized for any analogous device, method, or system—medical or otherwise.

The directional terms "proximal" and "distal," and their respective initials "P" and "D," are used to describe relative components and features of the present disclosure. Proximal refers to a position closer to the exterior of the body or a user, whereas distal refers to a position closer to the interior of the body or further away from the user. Appending the initials P or D to an element number signifies its proximal or distal location. Unless claimed, these directional terms and initials are provided for convenience and not intended to limit the present disclosure to a particular direction or orientation. As used herein, the terms "comprises," "comprising," "including," or the like, are intended to cover a non-exclusive inclusion, such that a device or method that comprises a list of elements does not necessarily include only those elements, but may include other elements not expressly listed or inherent thereto. Unless stated otherwise, the term "exemplary" is used in the sense of "example" rather than "ideal."

Figure 1:
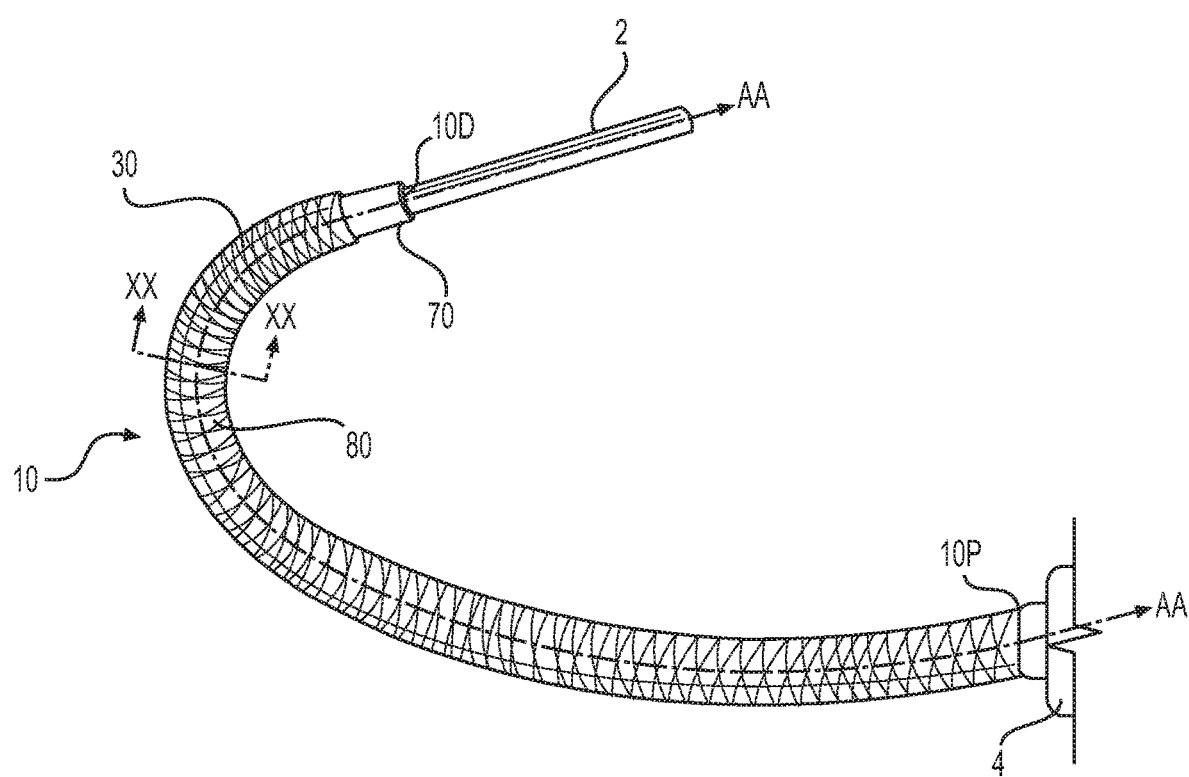
FIG. 1 depicts a perspective view of an articulating device, wherein an elongated object has been inserted through and steered by the device.
Figure 2:
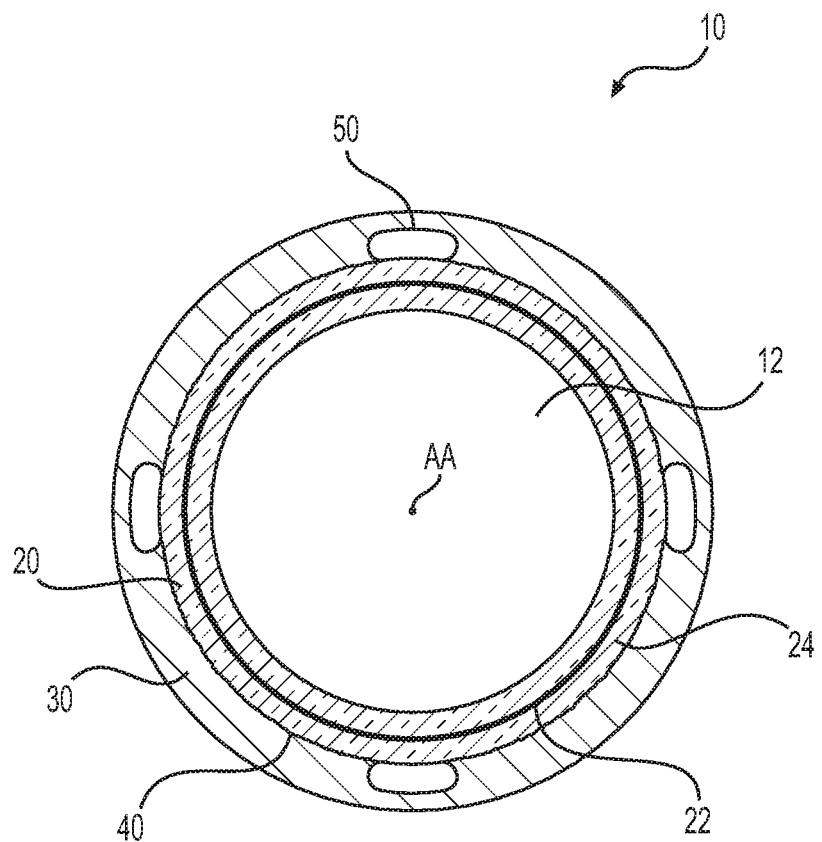
FIG. 2 depicts a section view of the device of FIG. 1 taken along line X-X.

One aspect of this disclosure is an articulating device 10 that extends along a central axis A-A between a distal end 10D and a proximal end 10P. Examples of device 10 are provided in FIGS. 1-5. As shown in FIG. 2, device 10 has thin wall comprising an interior core 20 attached to an exterior layer 30. The thin wall of device 10 has a thickness smaller than other steerable devices so that either: the outer diameter of device 10 may be reduced to promote insertion and/or tracking of device 10 through a body lumen; or the inner diameter of an interior lumen 12 of device 10 may be increased to maximize the usable interior space of device 10. For example, one or more elongated objects 2 may extend through interior lumen 12, or through one of a plurality of lumens 12 formed in device 10. In some aspects, object 2 may, for example, be an endoscope that extends through one lumen 12 and includes one or more working channels. Any of these working channels may house, for example, a laser fiber, such that device 10 may be articulated to steer (e.g., bend) a distal end of the laser fiber towards a kidney stone. Object 2 alternatively may be any type of diagnostic, surgical, or therapeutic device, any of which may be housed in lumen 12, or one of the plurality of lumens formed in lumen 12. The plurality of lumens my be separate from, and not overlap, each other, and therefore have parallel longitudinal axes.

FIG. 2 depicts aspects of device 10 with reference to a section cut X-X. As shown, interior core 20 is attached to exterior layer 30 by an interface 40. A plurality of lumens 50 may extend through layer 30 in a direction parallel to central axis A-A. Each lumen 50 may be configured to receive a steering wire 60 therethrough (e.g., FIG. 4). Interface 40 bonds interior core 20 to exterior layer 30 so that device 10 may be articulated, for example, by application of a force F to one or more of wires 60. Device 10 may be an integral component of various devices, such as one of a scope, forceps, a stent, or the like; or used to replace or supplant the sheath of an existing device, such as the sheath of a flexible endoscope, rendering it steerable.

Interior core 20 of FIGS. 1-5 is depicted as a composite tube comprising a reinforcing element 22 encased in a first material 24. In FIGS. 1-5, reinforcement element 22 is depicted as, for example, a wire coil spiraling along central axis A-A. Element 22 may be made of any high strength material, including one of a metal, a carbon fiber, a composite structure, and/or other high (e.g., shear and/or tensile) strength material. In some aspects, reinforcing element 22 may comprise one of a wire ribbon, a woven wire tube, a matrix of wire-like elements, or the like. First material 24 is depicted as a first polymeric material that is transparent, although any relatively flexible material may be used, transparent or otherwise. Reinforcing element 22 may be encased in first material 24 so that the interior diameter of lumen 12, and thus core 20, is defined by material 24.

First material 24 may be formulated to achieve a chemical or physical bond with reinforcing element 22 to maximize force transfer therebetween. For example, the geometric configuration and/or exterior surfaces of element 22 may be configured (e.g., roughened) to maximize surface area contact with material 24. Core 20 may be further optimized for strength. For example, although depicted as a spiral, a portion of reinforcing element 22 may be parallel with central axis A-A to provide core 20 with additional column strength and/or transverse to axis A-A to provide additional shear strength. In other examples, element 22 may comprise plurality of particles (e.g., a polymeric aggregate) suspended in material 24 to provide core 20 with additional compressive strength. Various discrete portions of element 22 also may be interconnected for additional torsional strength and/or kink resistance.

Figure 3A:
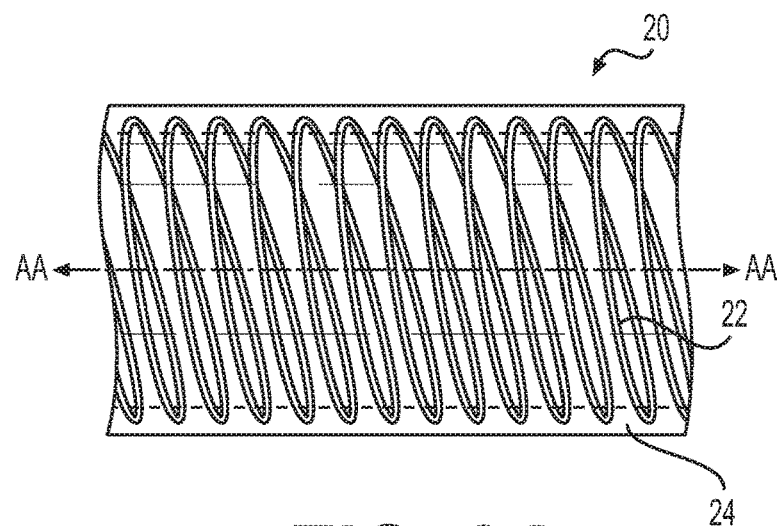
FIG. 3A depicts a side view of an interior core of the device of FIG. 1.
Figure 3B:
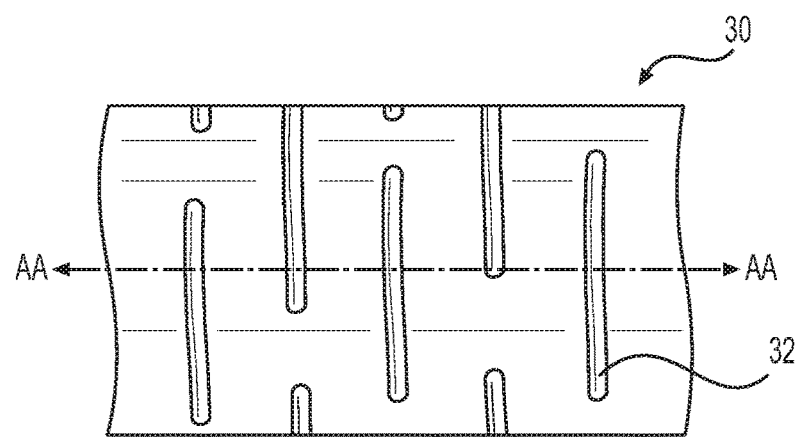
FIG. 3B depicts a side view of a exterior layer of the device of FIG. 3A.
Figure 3C:
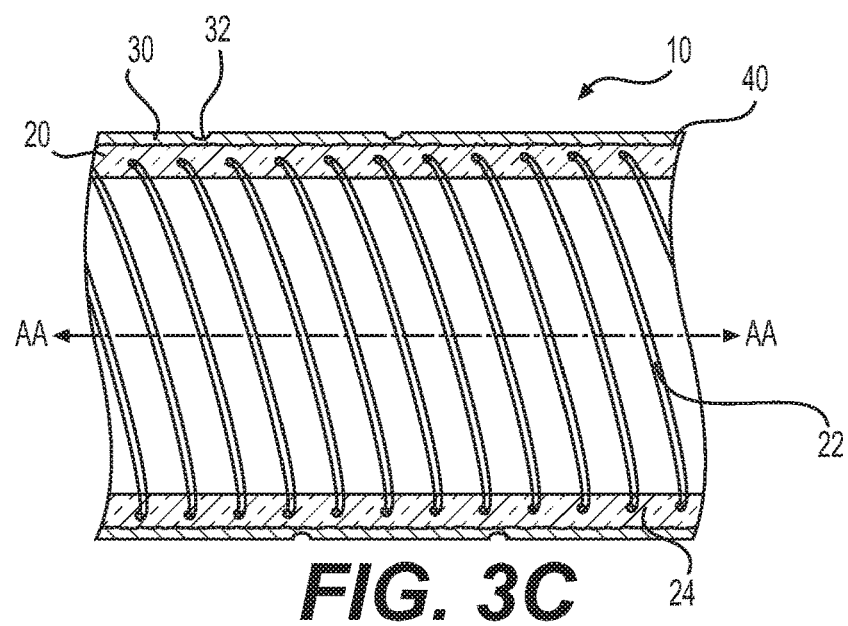
FIG. 3C depicts a section view of the exterior layer of FIG. 3B interfaced with the interior core of FIG. 3A.

Exterior layer 30 of FIG. 3B is formed of a second material that may be similar to or different from first material 24. In FIG. 3B, layer 30 is depicted as a semi-transparent tube made of a second polymeric material. A plurality of articulation slots 32 are defined by an exterior surface of layer 30 of FIG. 3B. Each slot 32 may, for example, be laser cut into layer 30 to define an articulating section 80 of device 10 (e.g., FIG. 1). In some aspects, each slot is circumferentially arranged and transverse with central axis A-A. Slots 32 create a stiffness differential in section 80 that adds localized flexibility thereto. As shown in FIG. 3C, exterior layer 30 may be attached to interior core 20 by interface 40, which may comprise any type of chemical or physical bond. In some aspects, interface 40 may be a physical bond formed by placing exterior layer 30 of FIG. 3B over interior core 20 of FIG. 3A, and applying heat to form device 10 of FIG. 3C, wherein an interior portion of layer 30 is fused (e.g., melded) with an exterior portion of core 20. In other aspects, interface 40 may be a chemical bond formed by application of, for example, an adhesive agent (e.g., a glue) that fuses layer 30 with core 20.

Each lumen 50 is formed in exterior layer 30 to receive a steering wire 60 therein. Device 10 may be articulated by applying force F to one or more of pull wires 60 in a direction parallel to central axis A-A until a portion of device 10 (e.g., a side) is deflected away from central axis A-A. Device 10 of FIG. 4, for example, has four lumens 50 organized oppositely at 90° intervals about central axis A-A to permit four-way deflection of the distal end 10D of device 10. Because each wire 60 is contained in one of lumens 50, applying force F to wires 60 may cause an axial component $F_A$ of force F to act in a direction parallel to central axis A-A, and a transverse component $F_T$ of force F to act in a direction transverse to axis A-A. Device 10 is configured to resolve these forces. For example, axial component $F_A$ may cause wire 60 to rub against the exterior surface of interior core 20. Reinforcing element 22 and/or layer 30 prevent wire 60 from sawing or cutting through a portion of device 10 in response to component $F_A$. As another example, transverse component $F_T$ may cause the interior portion of layer 30 to pull away from the exterior portion of core 20. The bond achieved by interface 40 prevents this result.

Because of interface 40, each lumen 50 may be disposed external of interior core 20 and reinforcing element 22, thereby maximizing the inner diameter of interior lumen 12 of device 10. Each lumen 50 may have a cross-sectional shape with a minimum dimension in a direction perpendicular to central axis A-A. Exemplary cross-sectional shapes may include a rectangle, a rounded rectangle, a curved rectangle, an oval, or the like, any of which may be configured (e.g., elongated or flattened) to maximize the inner diameter of lumen 12 by residing within layer 30. Each wire 60 also may be configured to maximize the inner diameter of lumen 12. For example, as shown in FIGS. 4 and 5, each wire 60 may have a cross-sectional shape similar to lumen 50, allowing each wire 60 to have a cross-sectional area equivalent to that of a circular wire, yet with a smaller minimum dimension.

Figure 4:
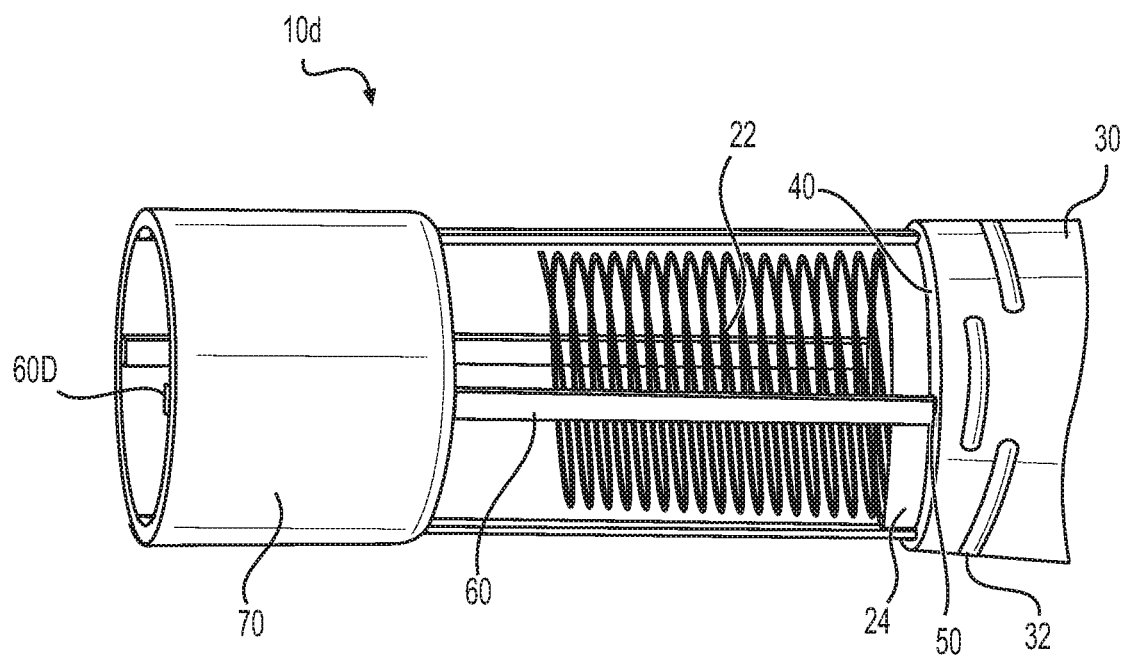
FIG. 4 depicts a deconstructed view of a distal end of the device of FIG. 1.
Figure 5:
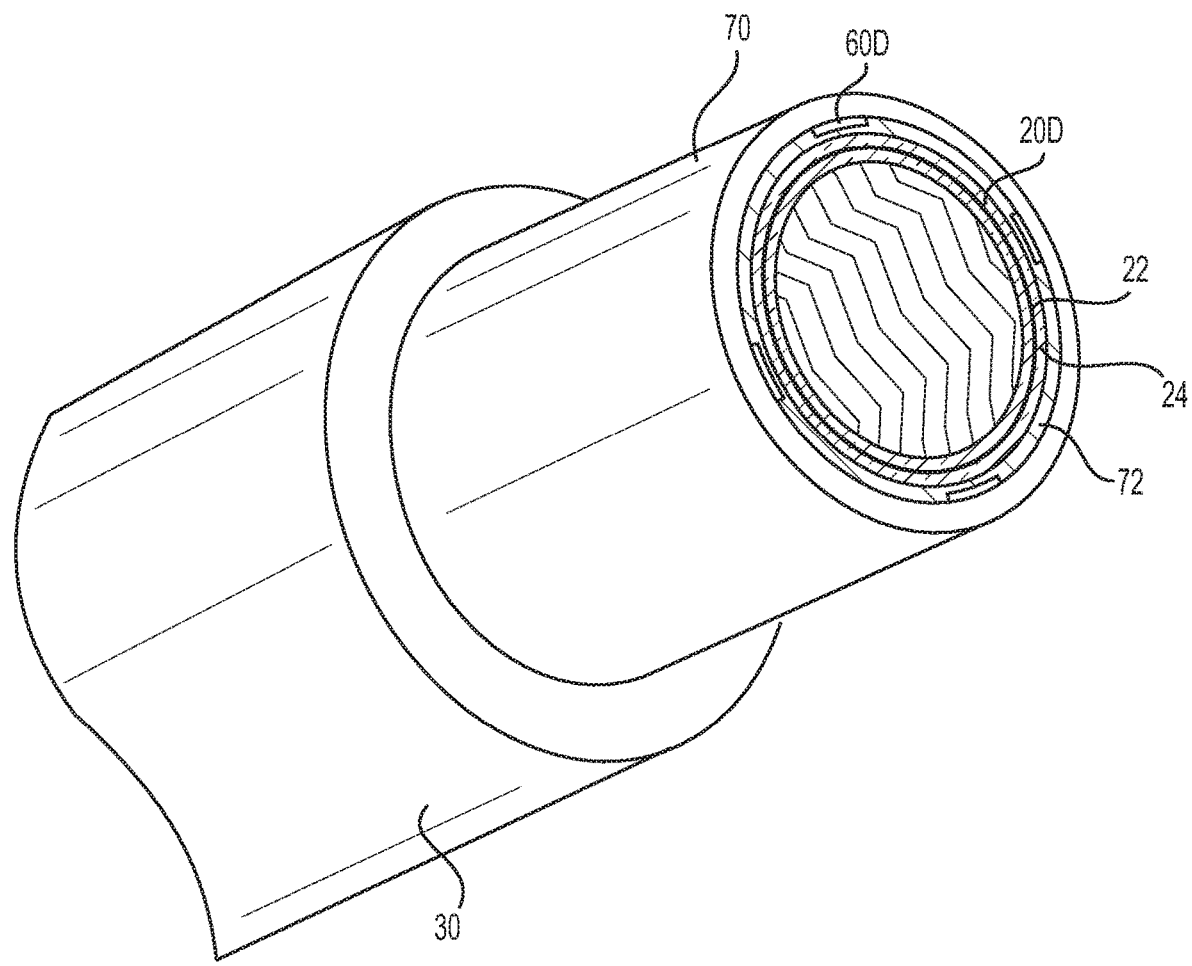
FIG. 5 depicts a perspective view of the distal end of the device of FIG. 1.

Distal end 10D of device 10 may have a cap 70, illustrated in FIGS. 4 and 5 as a metal ring. As shown in FIGS. 4 and 5, a distal end 60D of each steering wire 60 is attached (e.g., welded) to the interior surface of cap 70. In FIG. 5, cap 70 has been slid over a distal end 20D of interior core 20 to contain each wire 60 between the exterior surface of end 20D and the interior surface of cap 70. A filler material 72 (e.g., an epoxy) has been placed between each wire 60 to bond core 20, wires 60, and cap 70 at distal end 10D of device 10. This bond allows force F to be transferred from wires 60 to distal end 10D. A proximal-facing surface of cap 70 may abut a distal-facing surface of layer 30, as in the example of FIG. 5, to seal each lumen 50. A proximal end 60P of each steering wire 60 may be attached to a steering mechanism 4 located at proximal end 10P, as in FIG. 1. An exemplary mechanism 4 is disclosed in U.S. patent application Ser. No. 14/458,374, the entirety of which is hereby incorporated by reference into this disclosure. Alternatively, any suitable handle or steering mechanism known in the art, including knobs, levers, and the like, may be used as steering mechanism 4.

Figure 6A:
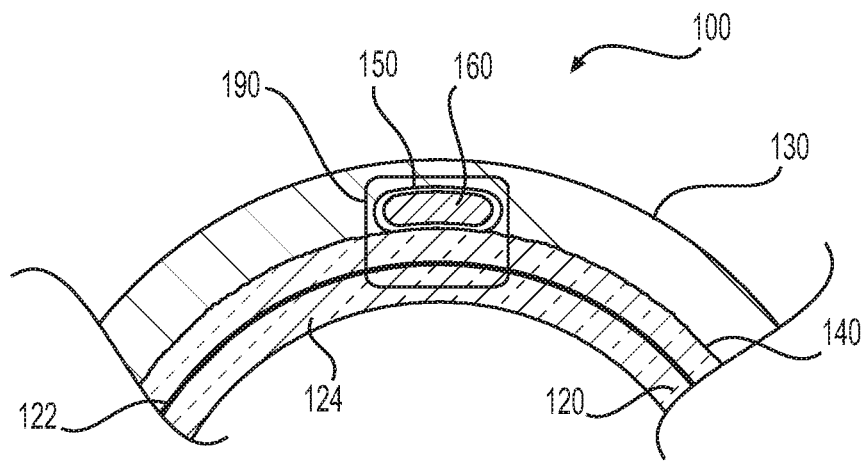
FIG. 6A depicts a section view of an alternate articulating device.
Figure 6B:
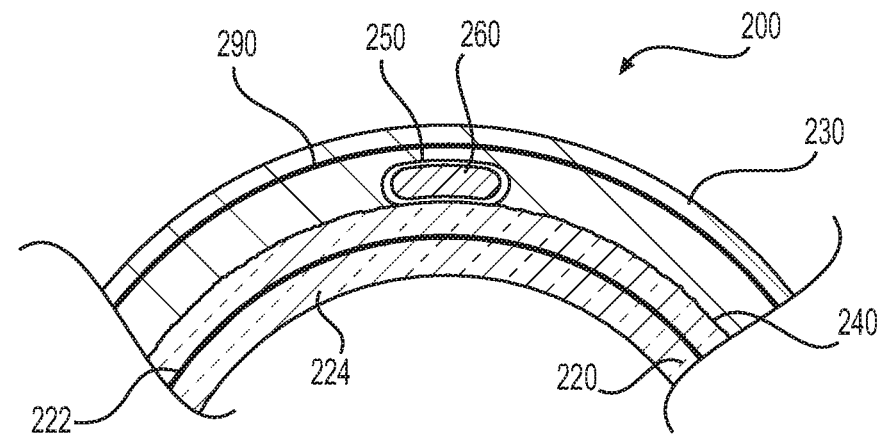
FIG. 6B depicts a section view of another alternate articulating device.
Figure 6C:
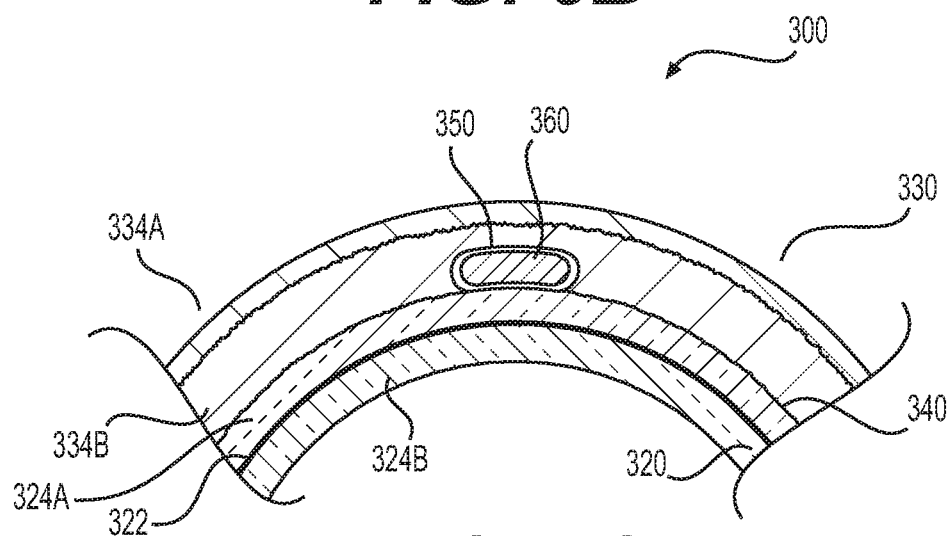
FIG. 6C depicts a section view of yet another alternate articulating device.

Additional aspects of articulation device 10 are illustrated in FIGS. 6A-C. Each aspect is now described with reference to an articulation device 100, 200, or 300. Wherever possible, like reference numbers have been used to described like elements for each alternative aspect of device 10, but within the respective 100, 200, or 300 series of numbers. Any additional aspect may be combined with any other aspect of device 10, each possible combination or iteration being part of this disclosure.

As shown in FIG. 6A, device 100 has an exterior layer 130 bonded to an interior core 120 by an interface 140. Core 120 comprises a reinforcing element 122 encased in a first material 124. A pull wire 160 extends through a lumen 150 in FIG. 6A. In contrast to device 10, device 100 further comprises a plurality of reinforcing bands 190 spaced apart in a direction parallel to central axis A-A. Each reinforcing band 190 surrounds a lumen 150 and is engaged (e.g., interwoven) with a portion of reinforcing element 122. Each band 190 may be made of the same material as reinforcing element 122. Although depicted as discrete elements, bands 190 may also be connected. For example, a plurality of band-like elements may be formed by encircling each lumen 150 with a spiraled wire interwoven with reinforcing element 122. This configuration ensures that the transverse component $F_T$ of force F is resolved by both interface 140 and reinforcing element 122. For example, each band 190 may prevent wire 160 from shearing through layer 130 in response to transverse component $F_T$.

Other aspects of this disclosure are shown in FIG. 6B, wherein device 200, similar to devices 10 and 100, has an exterior layer 230 bonded to an interior core 220 to define at least one lumen 250. In contrast to device 100, device 200 comprises a reinforcing element 290 encased in exterior layer 230. Reinforcing element 290 may be similar to or different from reinforcing element 22 of device 10. For example, reinforcing element 290 may be a spiraled wire or ribbon, a woven tube composed of the same, a matrix of wire-like elements, or the like; any of which may be made of a metal, a carbon fiber, a composite structure, or other high strength material. Reinforcing element 290 is radially outside of lumen 250 to, for example, prevent a wire 260 from shearing through exterior surface layer 230 in response to transverse component $F_T$. Because it surrounds core 220, element 290 may also increase the columnar and/or shear strength of device 210.

Still other aspects of this disclosure are shown with respect to device 300 of FIG. 6C. As before, device 300 has an exterior layer 330 bonded to an interior core 320 to define a lumen 350. Layer 330, like layer 30, may have a plurality of articulation slots formed (e.g., laser cut) therein. At least one of layer 330 and core 320 is a composite structure formed of more than one material. For example, an exterior portion of core 320 in FIG. 6C is formed of a first thermoplastic 324A with a melting point temperature $T_{324A}$, while an interior portion of core 320 is formed of a second thermoplastic 324B with a melting point temperature $T_{324B}$. Likewise, an exterior portion of layer 330 in FIG. 6C is formed of a first thermoplastic 334A having a melting point temperature $T_{334A}$, while an interior portion of layer 330 is formed of a second thermoplastic 334B having a melting point temperature $T_{334B}$. Melting point temperature $T_{334B}$ may be equal to melting point temperature $T_{324A}$ so that interface 340 is formed by application of heat to device 330. Moreover, melting point temperatures $T_{334A}$ and/or $T_{324B}$ may be greater than melting point temperatures $T_{334B}$ and/or $T_{324A}$ so that the articulation slots and/or lumen 312 of device 300 will not be deformed by the heat.

In still other aspects of device 300, a plurality of interior lumens may be formed in lumen 312. For example, second thermoplastic 324B may be formed to define a plurality of lumens extending through device 10 through interior lumen 12. Each of these exemplary lumens may be sized to house one or more elongated objects (e.g., object 2 of FIG. 1). For example, one of the plurality of lumens may be sized to receive an endoscope, while another lumen receives a laser fiber, and yet another lumen is used for aspiration. Because the driving wire 360 of device 300 is housed inside of lumen 350, outside of reinforcing element 322, each elongated object in any one of these plurality of lumens may be operated without interference from wire 360.

Figure 7:
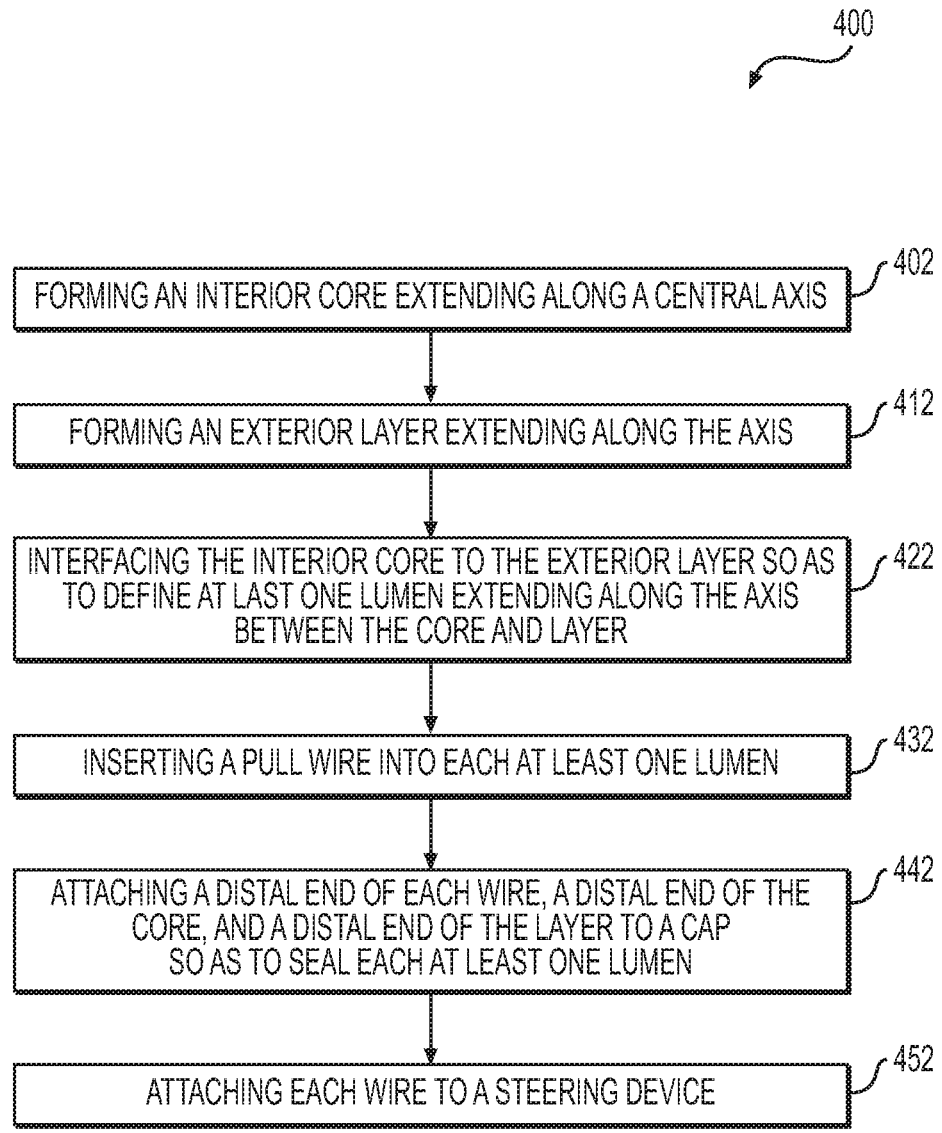
FIG. 7 depicts a method of manufacturing the devices of FIGS. 1-6C.

Another aspect of the present disclosure is a method 400 of manufacturing device 10. With slight modifications, as described below, method 400 may be used to make devices 10, 100, 200, and 300. An exemplary method 400 is depicted in FIG. 7 with respect to device 10. As shown, method 400 may comprise forming interior core 20 (402), forming exterior layer 30 (412), interfacing the core 20 to layer 30 so as to define central axis A-A within core 20 and at least one lumen 50 extending parallel to axis A-A between the core 20 and layer 30 (422), inserting a steering wire 60 into each at least one lumen 50 (432), and/or attaching the distal end 60D of each wire 60 to cap 70 (442). In some aspects, method 400 may further comprise attaching each wire 60 to steering device 4 (FIG. 1) (452).

Forming an interior core (402) may comprise co-extruding interior core 20. For example, a flow of first material 24 may be pushed through a mold together with a length of reinforcing element 22 so that element 22 is encased in core 20. This The length of interior core 20 may be varied, as needed, in method 400. Device 300 may also be formed by co-extrusion. For example, the method 400 (e.g., at 402) may be further modified to form core 320 by pushing materials 324A and 324B through a heated mold at a temperature equal to melting point temperatures $T_{324B}$, thereby bonding materials 324A and 324B to each other and/or reinforcing element 322.

The method 400 (e.g., at 412) may comprise extruding exterior layer 30. For example, a flow of polymeric material may be pushed through a mold to form a tube of any length. Slots 32 may be formed by applying laser energy to the exterior surface of an articulating section 80 of the tube (e.g., FIG. 1). For device 200, the method 400 may include a co-extrusion process, wherein the polymeric material is pushed through the mold together with reinforcing element 290 so that layer 230 encases element 290. For device 300, the method 400 may be modified for co-extrusion by pushing materials 334A and 334B through a heated mold at a temperature equal to melting point temperature $T_{334B}$, thereby bonding materials 334A and 334B to each other and/or reinforcing element 380. If interior lumen 312 is to define a plurality of lumens, the method 400 (e.g., at 412) may further comprise pushing an additional amount of the second material through a portion of the heated mold that is configured to produce the plurality of lumens.

Interface 40 may be formed by creation of a chemical or physical bond between the core 20 and layer 30. For example, the method 400 (e.g., at 422) may comprise applying an adhesive agent to the exterior surface of core 20 and/or the interior surface of layer 30, sliding core 20 into layer 30 along central axis A-A, and allowing the adhesive agent to cure, thereby fusing core 20 with layer 30. In other examples, core 20 may be slid into layer 30, and heat applied to core 20 and layer 30 to fuse the exterior surface of core 20 with the interior surface of layer 30. These aspects of method 400 may also be combined. For example, the adhesive agent may serve as both a lubricant that allows core 20 to be slid into layer 30, and a catalyst that, when heated, promotes fusion of core 20 with layer 30.

The plurality of lumens 50 may be formed in method 400 (e.g., at 422) by, for example, placing a plurality of elongated forms along the outside of core 20, and then sliding core 20 and the elongated forms into layer 30. Each form may be similar in shape to wire 60 and have a melting point temperature greater than $T_{334B}$ and/or $T_{324A}$. For example, each form may be made of metal. According to this aspect, heat may be applied to core 20 and layer 30 until a first interior portion of layer 30 is fused to an exterior portion of core 20, and a second interior portion of layer 30 is conformed around each elongated form to define each lumen 50. After removing the heat, each elongated form may then be removed. With devices 100 and 200, the method 400 may further comprise attaching the elongated forms to interior cores 120 or 220. For example, reinforcing bands 190 may be a staple with two forks that are pushed through the interior surface of core 120, in between spaces in reinforcing element 122, and out the exterior surface of layer 130. Each fork may then be folded over the elongated form, securing it to core 120. As further example, reinforcing element 290 of device 210 may be wrapped around core 220 and interwoven with reinforcing element 222 in order to secure the forms to core 220.

Once the lumens 50 have been defined, at least one wire 60 may be inserted into each lumen 50. The cross-sectional area of each lumen 50 is greater than the cross-sectional area of each wire 60, allowing each wire 60 to move inside of a lumen 50 in a direction parallel to central axis A-A. The method 400 (e.g. at 432) may additionally include applying a lubricant (e.g., a silicone-based coating) to, for example, the interior surfaces of each lumen 50 to ensure smooth operation of device 10. The distal end 60D of each wire 60 may be attached (e.g., welded) to the interior surface of cap 70, as shown in FIG. 5. The distal end 20D of core 20 may also be attached to the respective distal ends 60D of each wire 60 and the interior surface of cap 70 by, for example, inserting adhesive material 72 into the spaces between each distal end 60D. The distal end of exterior layer 30 may also be attached to cap 70 to, for example, seal each lumen 50.

In some aspects, the method 400 may be used to attach the proximal end 60P of each wire 60 to steering device 4. The proximal ends 20P and 30P of core 20 and layer 30 may also be attached to steering device 4 so as to seal each lumen 50 and any lubricants contained therein. For device 100, some aspects of method 400 may further comprise placing each reinforcing band 190 around one of the lumens 150. Each band 190 may, for example, be a staple with two forks that are pushed through the interior surface of core 120, out the exterior surface of layer 130, and folded into one of the slots 132. Alternatively, each band 190 may be a spiraled metal wire that is screwed into portions of core 120 and layer 130 to both surround a lumen 150 and interweave with reinforcing element 122, as shown in FIG. 6A.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. An articulating device comprising:
    an interior core with a reinforcing element extending along a central axis, wherein the reinforcing element is encased within the interior core;
    an exterior layer bonded to an exterior surface of the interior core by an interface;
    a lumen extending through the exterior layer, exterior of the reinforcing element, and parallel to the central axis; and
    a steering wire moveable in the lumen to articulate a distal end of the device relative to the central axis in response to a force applied to the wire;
    wherein an interior surface of the lumen includes a portion of the interior core and a portion of the exterior layer.

2. The device of claim 1, wherein the interface comprises a physical bond or a chemical bond formed between the exterior layer and the interior core.

3. The device of claim 1, wherein a plurality of articulation slots are defined by an exterior surface of the exterior layer.

4. The device of claim 1, wherein the reinforcing element spirals along a central axis of the articulating device.

5. The device of claim 4, wherein the interior core includes a first material, and the exterior layer includes a second material, and the interface comprises a fused portion of the first and second materials.

6. The device of claim 5, wherein an exterior portion of the exterior layer is made of a third material, an interior portion of the exterior layer is made of the second material, an exterior portion of the interior core is made of the first material, and the third material has a melting point greater than the melting point of the first and second materials.

7. The device of claim 4, wherein the reinforcing element comprises one or more wires spiraled about the central axis.

8. The device of claim 1, wherein the reinforcing element of the interior core is a first reinforcing element, the exterior layer comprises a second reinforcing element encased in the exterior layer, and the lumen is contained between an exterior surface of the interior core and an interior surface of the second reinforcing element.

9. The device of claim 8, wherein the second reinforcing element comprises a wire spiraled about the central axis to surround the interior core and the lumen, the wire being interwoven with a portion of the first reinforcing element.

10. The device of claim 1, further comprising at least one reinforcing band positioned around the lumen and engaged with the reinforcing element.

11. The device of claim 1, wherein the exterior layer is a first exterior layer, and the reinforcing element is a first reinforcing element, the device further comprising:
    a second exterior layer positioned radially outer from the first exterior layer relative to the central axis; and
    a second reinforcing element encased between the first exterior layer and the second exterior layer and positioned radially outer from the lumen relative to the central axis.

12. An articulating device comprising:
    an interior core extending along a central axis, the core including a first reinforcing element entirely encased therein;
    an exterior layer bonded to an exterior surface of the interior core by an interface, the exterior layer defining a plurality of articulation slots and including a second reinforcing element;
    a plurality of lumens extending through the exterior layer, external of the first reinforcing element, and parallel to the central axis; and
    a plurality of steering wires, each wire being moveable in one of the plurality of lumens to articulate a distal end of the device relative to the central axis in response to a force applied to one or more of the steering wires;
    wherein the second reinforcing element is encased within the exterior layer and is positioned radially-outer from the plurality of lumens relative to the central axis.

13. The device of claim 12, further comprising a cap attached a distal end of each of the plurality of wires.

14. The device of claim 13, wherein a distal end of interior core and a distal end of the exterior layer are attached to the cap to seal each of the plurality of lumens.

15. An articulating device comprising:
    an interior core with a reinforcing element extending along a central axis, wherein the reinforcing element is entirely embedded within the interior core;
    an exterior layer bonded to an exterior surface of the interior core by an interface;
    a lumen extending through the exterior layer, radially outward of the reinforcing element, and parallel to the central axis;
    a steering wire moveable in the lumen to articulate a distal end of the device relative to the central axis in response to a force applied to the wire; and at least one reinforcing band positioned around the lumen and the steering wire, wherein the reinforcing band is engaged with the reinforcing element.

16. The device of claim 15, wherein an interior surface of the lumen includes a portion of the interior core and a portion of the exterior layer.

17. The device of claim 15, wherein a plurality of articulation slots are defined by an exterior surface of the exterior layer.

18. The device of claim 15, wherein the reinforcing element spirals along the central axis; and wherein the at lease one reinforcing band includes a plurality of reinforcing bands.

19. The device of claim 15, wherein the interior core includes a first material, and the exterior layer includes a second material, and the interface comprises a fused portion of the first and second materials.

\* \* \* \* \*